United States Patent [19]

Takahashi et al.

[11] Patent Number: 4,626,089
[45] Date of Patent: Dec. 2, 1986

[54] OPHTHALMIC INSTRUMENT HAVING A FOCUS DETECTING SYSTEM

[75] Inventors: Susumu Takahashi; Kiwami Horiguchi, both of Tokyo, Japan

[73] Assignee: Tokyo Kagaku Kikai Kabushiki Kaisha, Tokyo, Japan

[21] Appl. No.: 594,675

[22] Filed: Mar. 29, 1984

[30] Foreign Application Priority Data

Apr. 2, 1983 [JP] Japan .................................. 58-58497

[51] Int. Cl.⁴ .............................................. A61B 3/14
[52] U.S. Cl. ..................................... 351/208; 351/206
[58] Field of Search ............... 351/206, 207, 208, 205; 354/62

[56] References Cited

U.S. PATENT DOCUMENTS 4,436,388  3/1984  Takahashi et al. .................. 351/208

FOREIGN PATENT DOCUMENTS 54-52895  4/1979  Japan .
57-125732  8/1982  Japan .

Primary Examiner—Rodney B. Bovernick
Attorney, Agent, or Firm—Brumbaugh, Graves, Donohue & Raymond

[57] ABSTRACT

An eyefundus camera including an observing and photographing optical system having a focusing lens, a mark projecting optical system for projecting a plurality of mark images on patient's eyefundus. The mark projecting optical system is interconnected with the focusing lens of the observing and photographing optical system. There is provided a focusing signal detecting device including a photoelectric device for photoelectrically scanning the mark images projected on the fundus of the patient's eye to produce mark image signals, a horizontal synchronizing signal counting circuit for counting horizontal synchronizing signals for the photoelectric means, a mark image counting circuit for counting number of the mark image signals to determine that a predetermined number of mark image signals exist in a single scanning line, an operation circuit responsive to outputs of the two circuits for determining a horizontal scanning line which is used for judgement of focus conditions.

6 Claims, 14 Drawing Figures

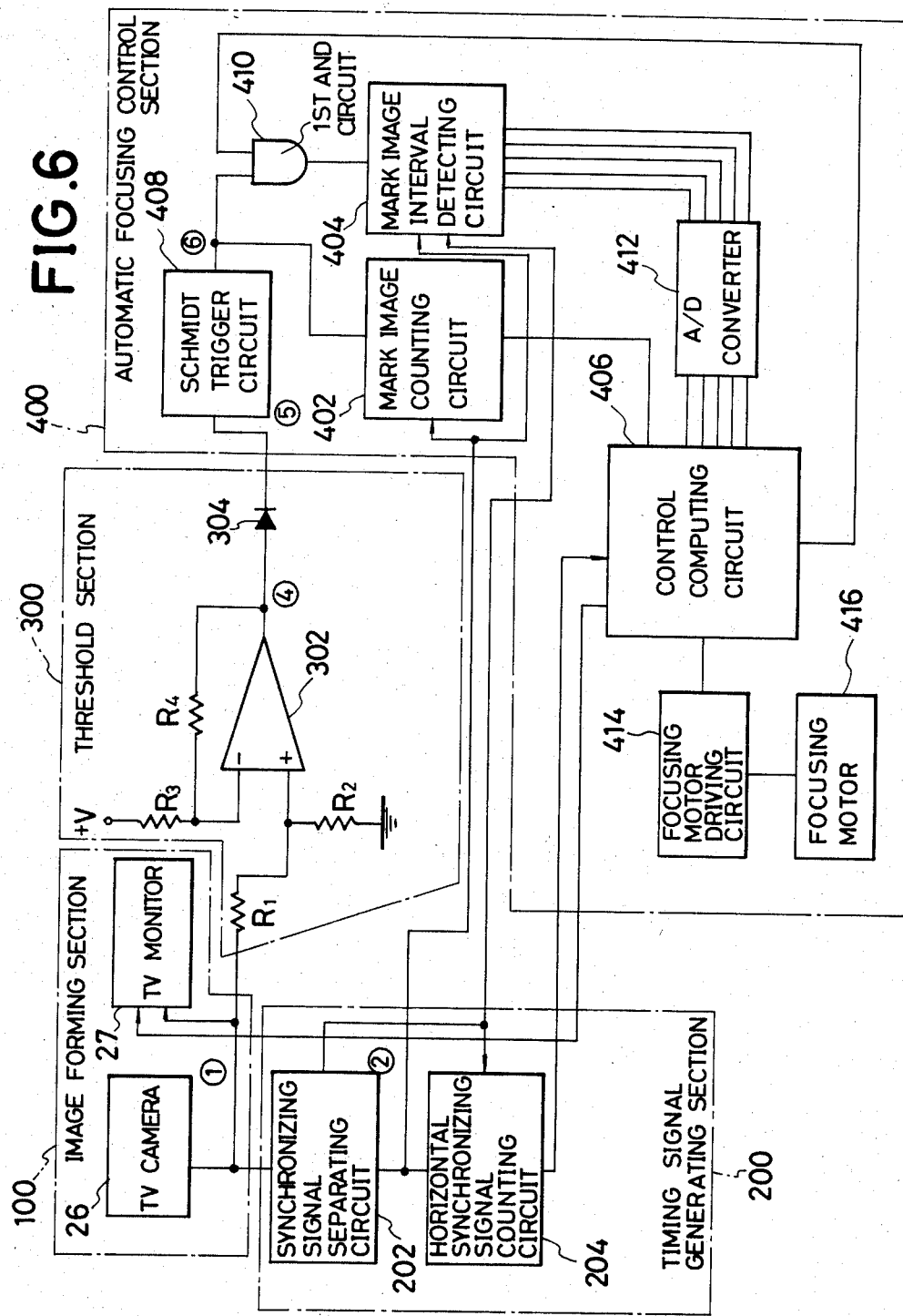

OPHTHALMIC INSTRUMENT HAVING A FOCUS DETECTING SYSTEM

The present invention relates to a focusing signal detecting device for ophthalmic instruments wherein a plurality of mark image are projected on the fundus of the patient's eye and the images are detected through a photoelectric scanning.

Conventionally, a focusing signal detecting device for this purpose has an image pick-up tube on which the eye fundus image is projected and scanned to produce scanning line signals. A preselected scanning line signal in then extracted in a standarized manner out of these scanning line signals and is compared with a predetermined reference level to effect an automatic focusing control. This type of focusing signal detecting devices are disclosed for example in Japanese Patent Laid-Open No. 52895/1979 laid open to public inspection on Apr. 25, 1979 and Japanese Patent Laid-Open No. 125732/1982 laid open to public inspection on Aug. 5, 1982.

In these known arts, however, valid scanning line signal is obtainable only when the mark images are projected correctly on predetermined positions on the eye fundus, so that a troublesome work is required for adjustment of alignment between an optical axis of the instrument and the image pickup tube. The alignment must be performed very precisely because, in order to permit a sufficient observation of the eyefundus and to eliminate distortion at end portions of the mark images due to a warp of the eyefundus, the size of the mark image on the eye fundus is limited.

It is therefore an object of the present invention to provide a focusing signal detecting device in which the aforementioned problems of prior can be eliminated.

Another object of the present invention is to provide a focusing signal detecting device for an ophthalmic instrument in which the instrument may not necessarily be aligned precisely with the patient's eye for an accurate focusing.

According to the present invention, the above and other objects can be accomplished by a focusing signal detecting device including projecting means for projecting a plurality of mark images to a fundus of a patient's eye, photoelectric means for photoelectrically scanning the mark images projected on the fundus of the patient's eye, a horizontal synchronizing signal counting circuit for counting horizontal synchronizing signals, a mark image counting circuit for counting number of the mark images to determine that a predetermined number of mark images exist, and means responsive to outputs of said two circuits for determining a horizontal scanning line which is used for judgement of focus conditions.

According to the features of the present invention, it becomes possible to increase the allowance for vertical deviations of the mark images on the eyefundus. Thus, the device of the present invention does not require a precise alignment between an optical axis of the instrument and the image pickup tube.

In order that the present invention be more clearly understood, descriptions will further be made with reference to a preferred embodiment taking reference to the accompanying drawings, in which;

FIG. 6 is a block diagram of an automatic focusing circuit;

Figure 1:
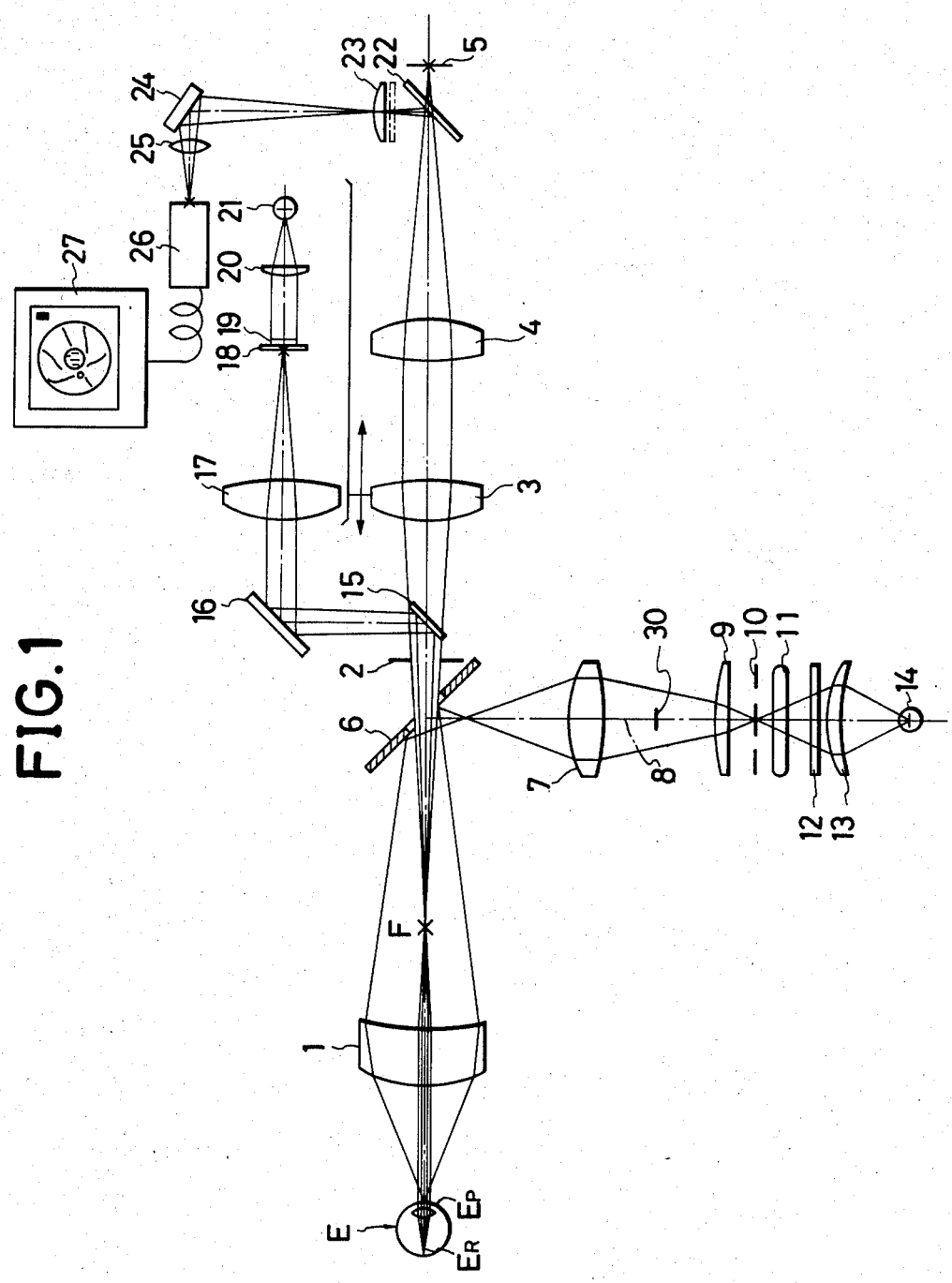
FIG. 1 is an illustration of the optical system for an eyefundus camera to which the invention can be applied.

Referring now to the drawings, particularly to FIG. 1, there is shown an optical system of an eyefundus camera to which the features of the present invention can be embodied. The optical system includes an observing and photographing optical system comprising an objective lens 1 opposing to a patient's eye E, an aperture 2 disposed on an optical axis of the lens 1 substantially in conjugate with the pupil Ep of the eye E with respect to the objective lens 1. Along the optical axis, there are also disposed a focusing lens 3, an image-forming lens 4 and a photographing film 5. An afocal optical system is formed by the focusing lens 3 and the image-forming lens 4. An image of the eyefundus $E_R$ is formed on the film 5 through this optical system. A slanted reflecting mirror 22 is disposed in front of the film 5 to reflect the light through the lens 4 upwards. A field lens 23 is disposed on the path of the light reflected by the mirror 22, at a point conjugate to the film 5. The light beam reflected by the mirror 22 and passed through the field lens 23 is focused on the photoelectric surface of an image pick-up tube 26, through a reflecting mirror 24 and focusing lens 25. The signal from the image pick-up tube 26 is sent to a monitor TV to form a visible image on the cathode ray tube of the TV.

An illuminating optical system is constituted by a perforated slant mirror 6 disposed in the photographing optic system just in front of the aperture 2 a relay lens 7, a condenser lens 9, a ring-shaped slit aperture 10, a flash tube 11 used as the photographing light source, a heat insulating filter 12, a focusing lens 13 and an observing illuminating light source 14. The light from the light source 14 impinges in a ring-like form upon the reflecting surface of the perforated mirror 6 and is reflected thereby to illuminate the eyefundus $E_R$ through the objective lens 1 and the pupil $E_P$.

Figure 2A:
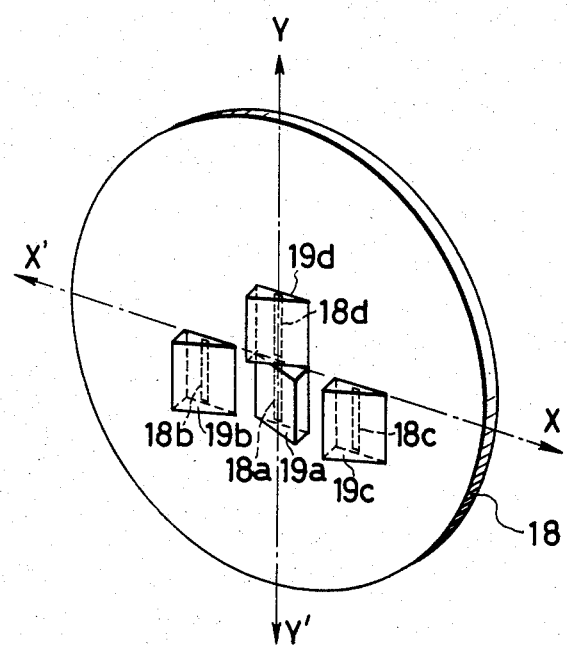
FIG. 2(a) is a perspective view of mark slits used in one embodiment of the invention.
Figure 2B:
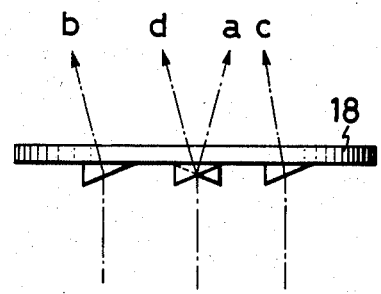
FIG. 2(b) is a plan view of the mark slits.
Figure 3:
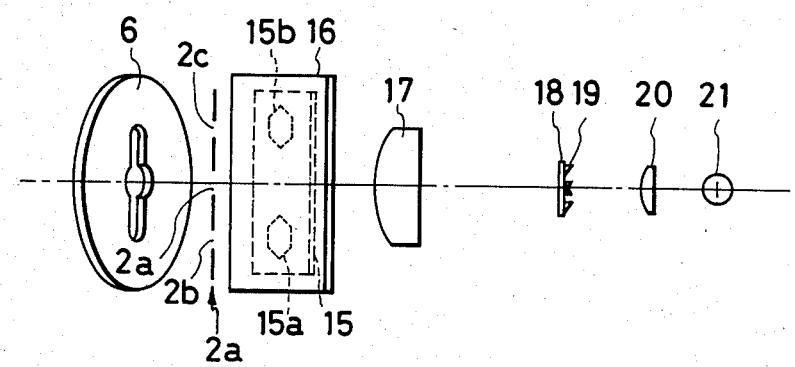
FIG. 3 is an illustration of an mark projecting optical system.

A mark projecting system has a slanted half-transparent mirror 15 disposed in the optical path of the photographing optical system behind the aperture 2, a reflecting mirror 16, a relay lens 17, a mark slit plate 18, deflecting prisms 19 disposed in close contact with the mark plate 18, a condenser lens 20 and a light source 21. The light from the light source 21 illuminates the mark plate 18 through the condenser lens 20. As will be seen from FIG. 2(a), the mark plate 18 includes mark slits 18a and 18d provided along the Y–Y' axis, and mark slits 18b and 18c parallel to the slits 18a and 18d and disposed at the opposite sides of the 18a with an equal distance therefrom. The deflecting prisms include prism elements 19a, 19b, 19c and 19d which are in close contact with the mark slits 18a, 18b, 18c and 18d, respectively. As will be seen from FIG. 2(b), the deflecting prisms 19a, 19b, 19c and 19d are adapted to deflect the light in the directions a, b, c and d in a plane containing the X-X' axis. The light beams passed through these slits form an image at a position F which is conjugate to the film 5 with respect to the lenses 3, 4 through the relay lens 17, the reflecting mirrors 16, 15, the aperture 2 and the perforation of the perforated mirror 6. The image at the point F is then projected to the eye E through the objective lens 1.

Thus, the light beams passed through the slits are divided by the deflection prisms 19 into beams of two directions which are projected symmetrically with respect to the optical axis. In order to reflect these light beams towards the objective lens 1, the reflecting mirror 15 disposed in the optical path of the photographing system is composed of a pair of reflecting portions 15a and 15b disposed at the opposite sides of the optical path. The reflecting mirror, therefore, does not hinder at all the effective light beam which is reflected by the eyefundus $E_R$ and passed towards the film 5. The aperture 2 also has a central aperture 2a for the photographing light beam and apertures 2b, 2c disposed at both sides of the central aperture 2a and adapted to pass the light beams transmitted through the slits, thereby to pass both of the photographing light beam which runs along the optical axis of the photographing optical system and the light beams which have passed through the slits. In order to pass the light beams from the slits, the perforation of the mirror 6 also has extensions at the opposite sides thereof.

In order to enhance the contrast of the mark slit images projected on the eyefundus $E_R$, it is preferred to shield the background illumination in the regions of projection. To this end, in this embodiment, a light shielding plate 8 of a size large enough to cover the mark images is arranged so as to be inserted into and extracted from the position conjugate to the eyefundus $E_R$.

In the optical system shown in FIGS. 1 and 2, the focusing operation is conducted by moving, along the optical axis, the focusing lens 3 as a unit with the constituents of the mark projecting system such as the release lens 17, mark slit plate 18, the deflection prisms 19, the condenser lens 20 and the light source 21. It is possible to detect the focusing condition on the film 5, through observing the mark slit images formed on the eyefundus $E_R$.

Figure 4:
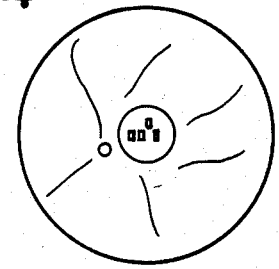
FIG. 4 is an illustration of an eyefundus image.
Figures 5A, 5B, 5C:
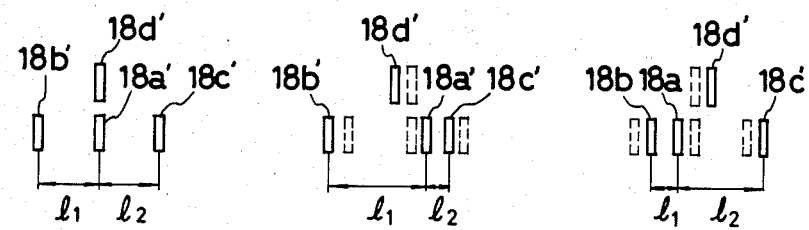
FIG. 5 is an illustration showing the relationship between the focusing condition and the mark slit images.

According to this arrangement, the mark images superposed to the eyefundus image are displayed on the monitor TV 27, as will be seen from FIG. 4. FIGS. 5(a) to 5(c) show the relationship between the focusing condition and the mark images. More specifically, FIG. 5(a) shows the mark images as obtained in the focused state, while FIGS. 5(b) and 5(c) show the mark images under out of focus. In FIGS. 5(b) and 5(c), broken lines show the positions of the mark images which would be obtained in the focused state. As the mark slit plane is moved along the optical path with respect to the eyefundus, the mark slit image 18a' move in the direction opposite to the direction of movement of the mark images 18b' and 18c'. In the focused state, the distance $l_1$ between the slit images 18b' and 18a' is equal to the distance $l_2$ between the slit images 18a' and 18c'. Thus, focusing is achieved by detecting the distance $l_1$ and $l_2$ electrically and moving the focusing lens 3 in the direction which is determined depending on whether the value $(l_1-l_2)$ is positive or negative. The focused state is detected through detection of the condition of $l_1=l_2$.

Figure 7:
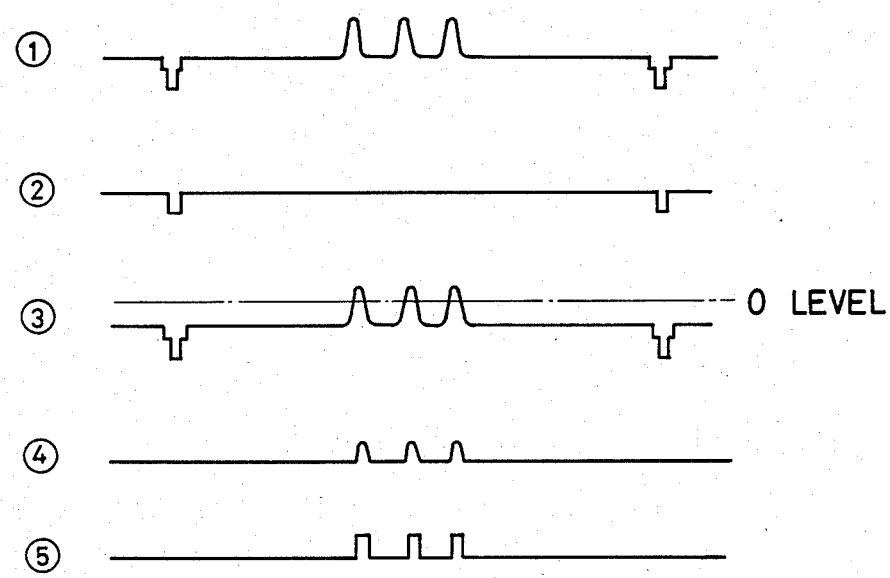
FIG. 7 is a waveform chart showing waveform of signals in the automatic focusing circuit shown in FIG. 6.

An explanation will be made hereinunder as to an automatic focusing circuit for effecting an automatic focusing operation through detection of the state of projection of the slit images, with specific reference to FIG. 6 showing the block diagram and FIG. 7 showing a waveform chart. The automatic focusing circuit is composed of an image forming section 100, a timing signal generating section 200, a threshold section 300 and an automatic focusing control section 400.

More specifically, the image forming section 100 is composed of a TV camera and a TV monitor 27. This section 100 permits an observation of the eyefundus image by means of the TV monitor 27 and delivers a mark image signal to the timing signal generating section 200 and the threshold section 300. Namely, the TV camera 26 produces an analogue output signal denoted by (1) in FIG. 7. The depressions appearing at both end portions of the signal curve represent the horizontal synchronizing signals, while three peaks appearing at the central portion correspond to the mark images.

The timing signal generating section 200 is composed of a synchronizing signal separating circuit 202 and a horizontal synchronizing signal counting circuit 204, and is adapted to deliver timing signals to other circuit blocks.

The synchronizing signal separating circuit 202 is adapted to extract the horizontal synchronizing signal and the vertical synchronizing signal from the output signal of the TV camera 26 which comprises both the image signals and the synchronizing signals. The extracted vertical synchronizing signal is delivered as a clearing signal to the horizontal synchronizing signal counting circuit 204 and a mark-image interval detecting circuit 404. The horizontal synchronizing signal is delivered to the horizontal synchronizing signal counting circuit 204, as well as to a mark-image counting circuit 402 and the mark-image interval detecting circuit 404 of the automatic focusing control section 400.

The horizontal synchronizing signal counting circuit 204 is adapted to count the number of the horizontal synchronizing signals and delivers the counted number to a control computing circuit 406 of the automatic focusing control section 400. The content of the horizontal synchronizing signal counting circuit 204 is cleared by the vertical synchronizing signal mentioned above. The control computing circuit 406, therefore, can identify the scanning signal which is being received, out of the scanning signals appearing on the monitor TV 27.

The threshold section 300 has first to fourth resistors $R_1$ to $R_4$, an operation amplifier 302 and a diode 304, and is adapted to extract and output the image signal, i.e. the mark image signal, from the output of the TV camera 26 which includes both the image signals and synchronizing signals.

The output from the TV camera 26 is grounded through the first and second resistors $R_1$ and $R_2$. The voltage produced by the second resistor $R_2$ is supplied to the positive terminal of the operation amplifier 302, while the negative terminal of the operation amplifier 302 is connected to the $+V$ terminal through the third resistor $R_3$ and also to the output terminal of the operation amplifier 302 through the fourth resistor $R_4$, whereby the differential amplification is conducted to amplify the difference between the output of the TV camera 26 and the voltage of the +V terminal.

As shown in (3) of FIG. 7, the voltage of the +V terminal and the resistance values of the first to fourth resistors $R_1$ to $R_4$ are selected such that all of the outputs from the operation amplifier OP is sliced by "0" level.

The output from the operation amplifier 302 is delivered to a diode 304 which cuts off the negative component of this output signal, so that a signal having only three central peaks corresponding to the index images is obtained as shown by (4) in FIG. 7. The output of the diode 304 is outputted to the Schmidt trigger circuit 408 of the automatic focusing control section 400.

The automatic focusing control section 400 is adapted to control the automatic focusing operation in accordance with the horizontal synchronizing signal and the counted number of the horizontal synchronizing signal delivered by the timing signal generating section 200, while counting the number of the index images from the index image signals delivered by the threshold section 300. The automatic focusing control section 400 includes the control computing circuit 406, Schmidt trigger circuit 408, a first AND circuit 410, the mark-image counting circuit 402, the mark-image interval detecting circuit 404, an A/D converter 412, a focusing motor driving circuit 414 and a focusing motor 416.

The Schmidt trigger circuit 408 is adapted to convert the analog mark image signal extracted from the threshold section 300 into rectangular waves as shown by (5) in FIG. 7. This output signal having rectangular waveform is delivered to the mark-image counting circuit 402 and also to the mark-image interval detecting circuit 404 through the first AND circuit 410.

The mark-image counting circuit 402 counts the mark-image pulses contained by the output signal from the Schmidt trigger circuit 408. The content of the counting circuit 402 is cleared by the horizontal synchronizing signal output from the synchronizing signal separating circuit 202 of the timing signal generating section 200, at each time the horizontal synchronizing signal is applied, so that the counting circuit 402 counts the number of the mark images between two successive horizontal synchronizing signals. The counting output from the circuit 402 is delivered to the control computing circuit 406.

A first AND circuit 410 selectively delivers the output of the Schmidt trigger circuit 408 to the mark-image interval detecting circuit 404 in accordance with the output from the control computing circuit 406.

Figure 8:
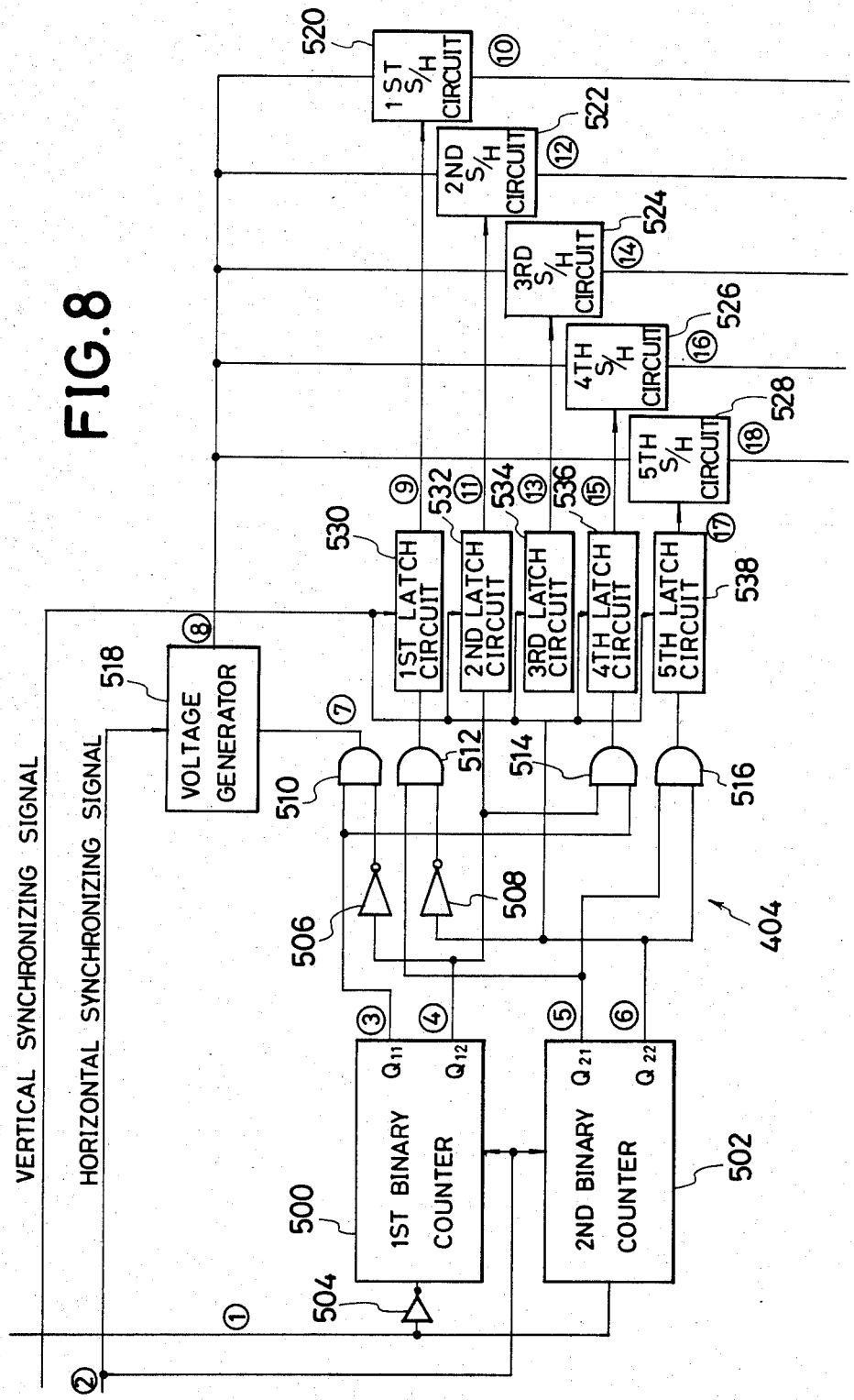
FIG. 8 is a block diagram of a mark image interval detecting circuit.

As will be seen from FIG. 8, the mark-image interval detecting circuit 404 has a first binary counter 500 adapted to conduct the counting at the time of all of the pulse, a second binary counter 502 adapted to conduct the counting at the time of fall of the counting, first to third NOT circuits 504, 506 and 508, second to fifth AND circuits 510, 512, 514, 516, a voltage generator 518, first to fifth sample hold circuits (referred to as S/H circuits, hereinunder) 520, 522, 524, 526, 528 and first to fifth latch circuits 530, 532, 534, 536, 538.

Figure 9:
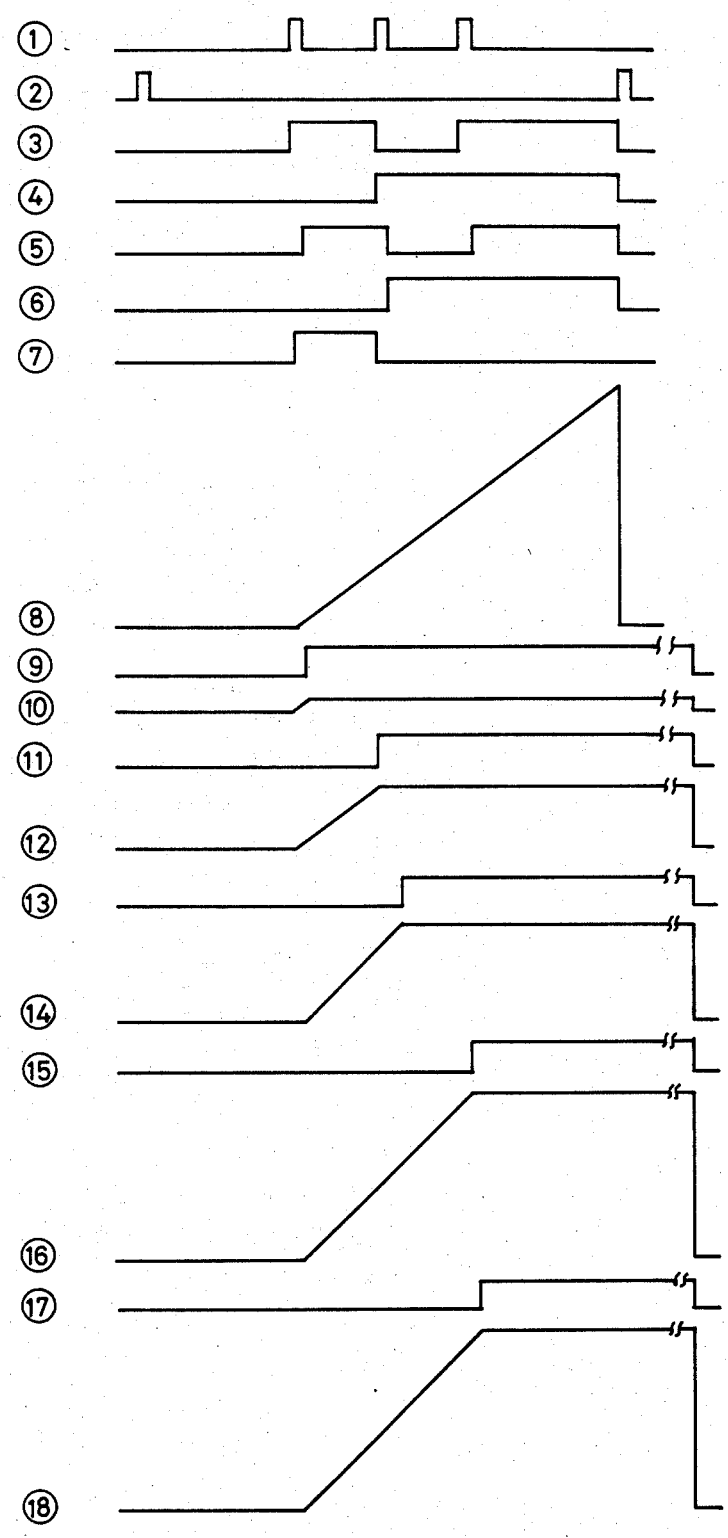
FIG. 9 is a waveform chart showing waveforms of signals in the mark image interval detecting circuit shown in FIG. 8.

In the mark-image interval detecting circuit 404 having the described construction, the mark-image signals having rectangular waveform designated at (1) in FIG. 9, outputted from the Schmidt trigger circuit 408, is delivered from the first AND circuit 410 to the first binary counter 500 through the first NOT circuit and also to the second binary counter 502 detouring the first NOT circuit. The first binary counter 500 conducts the counting of the pulse at the time of fall of the mark-image signal of rectangular waveform, and produces the lower digit from the terminal $Q_{11}$ thereof in the form of the signal designated at (3) in FIG. 9, while delivering the upper digit from the terminal $Q_{12}$ thereof in the form of the signal designated at (4) in FIG. 9.

On the other hand, the second binary counter 502 counts the pulses at the time of the same mark image signal and outputs the lower digits from the terminal $Q_{21}$ thereof in the form of signals denoted by (5) in FIG. 9, while delivering the upper digit from the terminal $Q_{22}$ thereof in the form of the signal denoted by (6) in FIG. 9.

The first binary counter 500 and the second binary counter 502 receive the horizontal synchronizing signal from the horizontal/vertical synchronizing signal separating circuit 202, and are reset at each time of receipt of the horizontal synchronizing signal.

The second AND circuit 510 receives the output derived from the terminal $Q_{11}$ of the first binary counter 500 designated at (3) in FIG. 7, as well as the output derived from the terminal $Q_{12}$ of the same designated at (4) in FIG. 7 after conversion by the second NOT circuit 506, and delivers an output which is the AND of these two signals to the voltage generator 518. This output is the signal designated at (7) in FIG. 9, having the form of pulse the rise of which represents the rise of the first mark image. This output received by the voltage generator 518 serves as the timing signal for determining the timing of commencement of generation of the voltage.

The voltage generator 518 includes a latch function so that it commences the generation of voltage at a timing conforming with the timing of rise of the first mark image, and continues to generate the voltage which is increased with a good linearity as designated at (8) in FIG. 9. This voltage is delivered to the first to fifth S/H circuits 520, 522, 524, 526, 528. The voltage generator 518 receives, as the clearing signal, the horizontal synchronizing signal designated at (2) in FIG. 9 derived from the signal separating circuit 202, as well as the horizontal/vertical synchronizing signals. As the clearing signal is received, the voltage generator stops to generate the voltage so that the output voltage becomes zero.

The timing signals for the first to fifth S/H circuits 520 to 528 are formed by the first to fifth latch circuits 530 to 538, respectively. The latch circuits 530 to 538 receive, as the unlatching signal, the vertical synchronizing signal from the horizontal/vertical synchronizing signal separating circuit 202, so that they continue the latching until the vertical synchronizing signal is received.

The first S/H circuit 520 operates in accordance with the timing signal which is the output from the first latch circuit 520, i.e. the AND of the output of the terminal $Q_{21}$ of the second binary counter 502 and the output from the terminal $Q_{22}$ of the same inverted by the third NOT circuit 508, the AND being produced by the third AND circuit 512 and latched as the signal indicated at (9) in FIG. 9. The first S/H circuit 520 has the holding term corresponding to the portion H of the timing signal so that it holds the voltage corresponding to the interval between the rise and fall of the first mark image signal shown by (10) in FIG. 9.

The second S/H circuit 522 operates in accordance with the timing signal which is the output from the second latch circuit 532, i.e. the output (shown by (4) in FIG. 9) from the terminal $Q_{12}$ of the second binary counter 500 latched as the signal indicated at (11) in FIG. 9. This signal rises at the time of rise of the second mark image signal. The second S/H circuit 522 has the holding period corresponding to the portion H of the timing signal so that it holds the voltage corresponding to the interval between the rise of the first mark image signal and the rise of the second mark image signal.

The third S/H circuit 524 operates in accordance with the timing signal which is the output from the third latch circuit 534, i.e. the output (shown by (6) in FIG. 9) from the terminal $Q_{22}$ of the second binary counter 502 which rises at the time of fall of the second mark image signal and is latched as the signal indicated at (13) in FIG. 9. This signal rises at the time of fall of the second mark image signal. The third S/H circuit 524 has the holding period corresponding to the portion H of the timing signal so that it holds the voltage corresponding to the interval between the rise of the first mark image and the fall of the second mark image, as shown by (14) in FIG. 9.

The fourth S/H circuit 526 operates in accordance with the timing signal which is the output from the fourth latch circuit 536, i.e. the AND of the output from the terminal $Q_{11}$ of the first binary counter 500 which rises at the time of rise of the third mark signal and the output from the terminal $Q_{12}$ of the same, the AND being produced by the fourth AND circuit 514 and latched as the signal indicated at (15) in FIG. 9. This signal rises at the time of rise of the third mark image signal. The fourth S/H circuit 526 has the holding period which corresponds to the portion H of the timing signal so that it holds the voltage corresponding to the interval between the rise of the first image signal and the rise of the third image signal, as shown by (16) in FIG. 9.

The fifth S/H circuit 528 operates in accordance with the timing signal which is the output from the fifth latch circuit 538, i.e. the AND of the outputs from the terminals $Q_{21}$ and $Q_{22}$ of the secondary binary counter 502 produced by the fifth AND circuit 516 and latched as the signal (17) in FIG. 9. This signal rises at the time of fall of the third mark image signal. The fifth S/H circuit 528 has a holding period corresponding to the portion H of the timing signal so that it holds the voltage corresponding to the interval between the rise of the first mark image signal and the fall of the third mark image signal, as shown by (18) in FIG. 9.

Since the first to fifth S/H circuits 520 to 528 make use of the outputs from the first to fifth latch circuits 530 to 538, respectively, they continue the holding until the vertical synchronizing signal is received, thereby to preserve the processing time for the processing performed by the A/D converter 412.

The A/D converter 412 which receives the outputs from the first to fifth S/H circuits 520, 522, 524, 526, 528 operates to convert respective analog input voltage signals into digital voltages which are then delivered to the control computing circuit 406.

The control computing circuit 406 receives the outputs from the horizontal synchronizing signal counting circuit 204 of the timing signal generating section 200, the mark image counting circuit 402 and the A/D converter 412. Upon receipt of these signals, the control computing circuit 406 delivers a focusing signal to the TV monitor 27, a gate signal to the first AND circuit 410 and, through the focusing motor driving circuit 414, a focusing control signal to the focusing motor 416.

Figure 10:
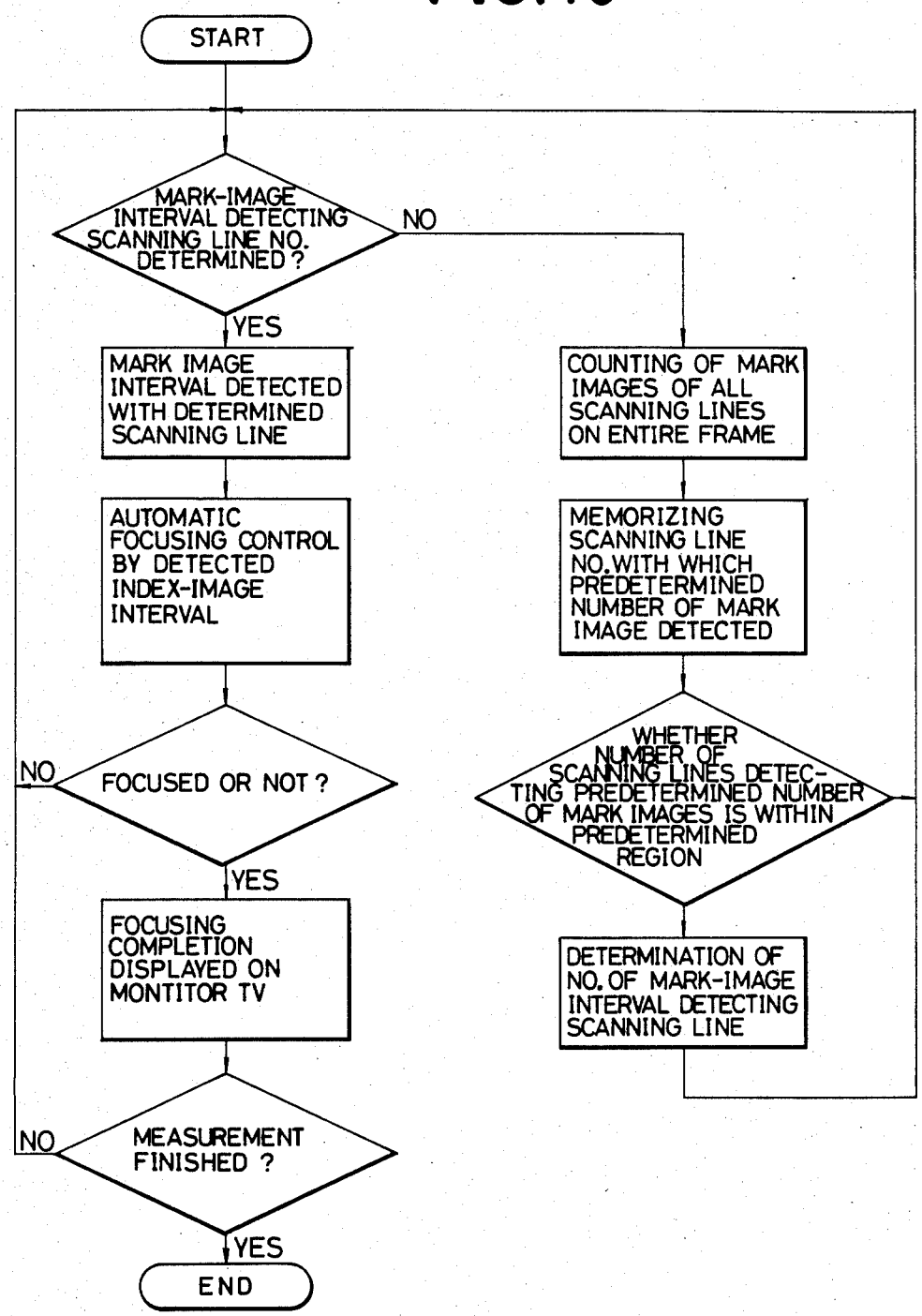
FIG. 10 is a chart showing the control routine of the control computing circuit.

The control routine of the control computing circuit 406 is shown in FIG. 10. As the ophthalmic instrument starts to operate, a judgement is made as to whether the scanning line for detecting the mark-image interval has been determined. The scanning line has not been determined yet at the time of the first judgement, so that the mark image counting circuit 402 counts the number of the mark images of all scanning lines over the entire frame. Then, the number of the horizontal scanning line, with which a predetermined number, e.g. 3 (three), of the mark images is detected is memorized.

Figure 11:
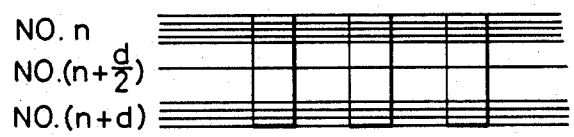
FIG. 11 is an illustration of the relationship between the mark images and the scanning lines.

Since the mark image is vertically elongated as shown in FIG. 11, a plurality of successive scanning lines, for example, n th to (n+d)th line detect the predetermined number of mark images. Considering that the length of the mark image varies depending on the state of focusing, a predetermined range of image length is assumed. Namely, if the number d of the successive scanning lines which have detected the predetermined number of mark images falls within the thus assumed region, these images are recognized as the mark images. However, if the number d falls out of the above-mentioned region, these images are not decided as being the mark images. When the mark images are recognized in the manner explained above, an operation is made to determine the number of the scanning line for detecting the interval between adjacent mark images. It is considered that the scanning line intersecting the mark image at the center of the latter detects the width of the mark image most precisely. The control computing circuit, therefore, determines the scanning line given by $(n+n+d)/2=n+d/2$ as the detecting scanning line.

Then, a judgement is made again as to whether the scanning line for detecting the mark image interval. At this time, since the scanning line has been determined already, the mark image interval is detected in accordance with the following procedure. Namely, the control computing circuit 406 compares the output from the horizontal synchronizing signal counting circuit 204 and the number of the determined detecting scanning line and, when they coincide with each other, outputs an H signal corresponding to one scanning line to the first AND circuit as the control signal. In accordance with this output, the mark image signal which is the output of the Schmidt trigger circuit 408 is applied to the mark image interval detecting circuit 404 thereby to conduct the detection of the interval between adjacent mark images.

Since flares are liable to be formed at the upper and lower ends of the frame, it is advisable not to use the signals of scanning lines corresponding to the upper and lower portions of the frame, in order to obviate any error which may be caused by the flare. This can be achieved simply by replacing the block "counting of mark images of all scanning lines over the entire area of frame" appearing in the flow chart in FIG. 10 by "counting of mark images of scanning lines on the frame other than the scanning lines constituting the upper and lower end portions of the frame".

The analog voltage signals AVa, AVb, AVc, AVd and AVe detected and held by the first to fifth S/H circuits 520, 522, 524, 526, and 528 are converted by the A/D converter 412 into digital voltage signals DVa, DVb, DVc, DVd and DVe. The distance of interval $l_1$ between the centers of the first and second mark images is determined by the following formula.

$$l_1 = \tfrac{1}{2}(DVb + DVc - DVa)$$

On the other hand, the distance of interval $l_2$ between the second and the third mark images is determined by the following formula.

$$l_2 = \tfrac{1}{2}(DVd + DVe - DVb - DVc)$$

Then, a calculation is made to determine $l = l_1 - l_2$. The direction of adjusting movement of the focusing lens 3 is determined in accordance with the nature of the difference 1, i.e. depending on whether the difference 1 is positive or negative, and the focusing is conducted by operating the focusing motor 46 in accordance with the value of the difference 1.

Then, a judgement is made as to whether the focused state has been obtained, i.e. whether the condition of $l_1 = l_2$ is met. When the focused state is obtained, i.e. when the condition $l_1 = l_2$ is met, a sign of a rectangular form representing the completion of focusing is put on the right upper corner of the frame on the monitor TV shown in FIG. 1. If the condition $l_1 = l_2$ is not met, the control computation explained hereinbefore is repeated.

The invention has thus been shown and described with reference to a specific example, however, it should be noted that the invention is in no way limited to the details of the illustrated arrangements but changes and modifications may be made without departing from the scope of the appended claims.

What is claimed is:

1. A focusing signal detecting device for an ophtalmic instrument including mark projecting means for protecting a plurality of mark images to a fundus of a patient's eye, photoelectric means for photoelectrically scanning the mark images projected on the fundus of the patient's eye by a succession of parallel scanning lines to produce mark image signals, a synchronizing signal counting circuit for counting line synchronizing signals for the photoelectric means, a mark image counting circuit for counting the number of mark image signals produced by the photoelectric means in each line scan to determine that a predetermined number of mark image signals exist in a single scanning line, means responsive to outputs of said two circuits for determining that said mark image signals occur in a plurality of successive scanning lines, and means for selecting one of said last named successive lines for judgment of focus condition.

2. A focusing signal detecting device in accordance with claim 1 in which the last mentioned means includes operation means for selecting one scanning line from a plurality of scanning lines in which said predetermined number of mark image signals are detected so as to use said one scanning line for judgement of focus conditions.

3. A focus signal detecting device in accordance with claim 2 in which said operation means includes means for selecting a central scanning line among said plurality of scanning lines.

4. A focus signal detecting device in accordance with claim 1 which further includes a mark signal interval detecting circuit for detecting intervals of the mark image signals in said horizontal scanning line determined by the last mentioned means.

5. A focus signal detecting device in accordance with claim 4 which further includes focusing means for effecting focusing of the instrument in accordance with the intervals of the mark images detected by the mark signal interval detecting circuit.

6. An ophthalmic instrument including an observation optical system having focusing lens means mark projecting means for projecting a plurality of mark images to a fundus of a patient's eye, photoelectric means for photoelectrically scanning the mark images projected on the fundus of the patient's eye to produce mark image signals, a horizontal synchronizing signal counting circuit for counting horizontal synchronizing signals for the photoelectric means, a mark image counting circuit for counting the number of the mark image signals to determine that a predetermined number of mark image signals exist in a single scanning line, means responsive to outputs of said two circuits for determining a horizontal scanning line which is used for judgment of focus conditions, a mark signal interval detecting circuit for detecting intervals of the mark image signals in said horizontal scanning line determined by the last mentioned means focusing means for effecting focusing of the instrument in accordance with the intervals of the mark images detected by the mark signal interval detecting circuit.

* * * * *